US011235156B2

(12) United States Patent
Romine et al.

(10) Patent No.: US 11,235,156 B2
(45) Date of Patent: Feb. 1, 2022

(54) WEARABLE AUDIO DEVICE WITH VAGUS NERVE STIMULATION

(71) Applicant: Bose Corporation, Framingham, MA (US)

(72) Inventors: Stephen L. Romine, Framingham, MA (US); John Trotter, Sudbury, MA (US)

(73) Assignee: Bose Corporation, Framingham, MA (US)

( * ) Notice: Subject to any disclaimer, the term of this patent is extended or adjusted under 35 U.S.C. 154(b) by 156 days.

(21) Appl. No.: 16/567,084

(22) Filed: Sep. 11, 2019

(65) Prior Publication Data

US 2021/0069505 A1 Mar. 11, 2021

(51) Int. Cl.
*A61N 1/36* (2006.01)
*A61N 1/04* (2006.01)

(52) U.S. Cl.
CPC ......... *A61N 1/3615* (2013.01); *A61N 1/0456* (2013.01); *A61N 1/36036* (2017.08)

(58) Field of Classification Search
CPC ............... A61N 1/3615; A61N 1/0456; A61N 1/36036; A61B 5/377; A61B 5/0004; A61B 5/7267; A61B 5/6817; A61B 5/02055; A61B 2560/0425; A61B 5/395; A61B 5/318; A61B 5/4836; A61B 5/0533; A61B 5/165
See application file for complete search history.

(56) References Cited

U.S. PATENT DOCUMENTS

| 4,503,863 | A  | 12/1985 | Katims |
| 7,613,519 | B2 | 11/2009 | De Ridder |
| 7,725,195 | B2 | 5/2010  | Lima et al. |
| 7,797,042 | B2 | 9/2010  | Dietrich et al. |
| 8,262,717 | B2 | 9/2012  | Rogers et al. |

(Continued)

FOREIGN PATENT DOCUMENTS

| CN | 103908747 B | 7/2014 |
| CN | 103961794 A | 8/2014 |

(Continued)

OTHER PUBLICATIONS

International Search Report and the Written Opinion of the International Searching Authority, International Patent Application No. PCT/US2020/050331, pp. 1-10, dated Nov. 25, 2020.

(Continued)

*Primary Examiner* — Catherine M Voorhees
(74) *Attorney, Agent, or Firm* — Bond, Schoeneck & King, PLLC (57) ABSTRACT

A method of providing vagus nerve stimulation (VNS) to a user is provided. The method includes the steps of: (1) collecting, by one or more sensors monitoring a user, one or more sets of physiological data; (2) determining, by a controller, an occurrence of a physiological event based on the one or more sets of physiological data; (3) stimulating, by a first earpiece worn by a user, a vagus nerve of the user with a VNS signal generated based on the controller determining the occurrence of the physiological event, wherein the VNS signal has an amplitude. The physiological condition may be an anxiety attack. The physiological condition may be a migraine headache.

20 Claims, 3 Drawing Sheets

(56) References Cited

U.S. PATENT DOCUMENTS

| | | |
|---|---|---|
| 8,506,469 B2 | 8/2013 | Dietrich et al. |
| 8,591,419 B2 | 11/2013 | Tyler |
| 8,666,501 B2 | 3/2014 | Kilgard et al. |
| 8,696,724 B2 | 4/2014 | Rogers |
| 8,885,861 B2 | 11/2014 | Beck et al. |
| 9,333,334 B2 | 5/2016 | Jeffery et al. |
| 9,610,443 B1 | 4/2017 | Dean et al. |
| 9,782,584 B2 | 10/2017 | Cartledge et al. |
| 2003/0195588 A1* | 10/2003 | Fischell ............... A61N 2/02 607/55 |
| 2006/0058854 A1* | 3/2006 | Abrams ............ A61N 1/36082 607/45 |
| 2007/0027504 A1 | 2/2007 | Barrett et al. |
| 2008/0021517 A1 | 1/2008 | Dietrich |
| 2008/0051852 A1 | 2/2008 | Dietrich et al. |
| 2010/0057154 A1 | 3/2010 | Dietrich et al. |
| 2011/0130615 A1 | 6/2011 | Mishelevich |
| 2011/0178442 A1 | 7/2011 | Mishelevich |
| 2013/0066350 A1 | 3/2013 | Mishelevich |
| 2014/0067021 A1 | 3/2014 | Rezai et al. |
| 2014/0142669 A1 | 5/2014 | Cook et al. |
| 2015/0126802 A1 | 5/2015 | Lim et al. |
| 2016/0279435 A1* | 9/2016 | Hyde ................. A61H 23/02 |
| 2016/0287898 A1 | 10/2016 | Smith et al. |
| 2016/0346545 A1 | 12/2016 | Pal et al. |
| 2017/0027812 A1 | 2/2017 | Hyde et al. |
| 2017/0143550 A1 | 5/2017 | Kilgard et al. |
| 2017/0151436 A1 | 6/2017 | Flaherty et al. |
| 2017/0368329 A1 | 12/2017 | Tyler et al. |
| 2018/0001077 A1 | 1/2018 | Cook et al. |
| 2018/0169411 A1 | 6/2018 | Goodall et al. |
| 2018/0169412 A1 | 6/2018 | Goodall et al. |
| 2018/0193641 A1 | 7/2018 | Black et al. |
| 2018/0200522 A1 | 7/2018 | Taca, Jr. |
| 2018/0250511 A1 | 9/2018 | Black et al. |
| 2018/0339148 A1* | 11/2018 | Kong ................... A61M 21/00 |
| 2019/0001117 A1* | 1/2019 | Ben-David .......... A61B 5/4836 |
| 2019/0001129 A1* | 1/2019 | Rosenbluth .......... A61N 1/0476 |

FOREIGN PATENT DOCUMENTS

| | | |
|---|---|---|
| CN | 104055625 A | 9/2014 |
| CN | 203915230 U | 11/2014 |
| CN | 107041809 A | 8/2017 |
| CN | 107041810 A | 8/2017 |
| CN | 206660005 U | 11/2017 |
| CN | 107970087 A | 5/2018 |
| DE | 202015007965 U1 | 12/2015 |
| EP | 2776121 A1 | 9/2014 |
| EP | 3377012 A1 | 9/2018 |
| KR | 101468355 B1 | 12/2014 |
| KR | 101724560 B1 | 4/2017 |
| WO | 2009039294 | 3/2009 |
| WO | 2012139603 A1 | 10/2012 |
| WO | 2012168543 A1 | 12/2012 |
| WO | 2016176668 A1 | 11/2016 |
| WO | 2016196635 A2 | 12/2016 |
| WO | 2017171219 A1 | 10/2017 |
| WO | 2017173331 A1 | 10/2017 |
| WO | 2018111997 A2 | 6/2018 |
| WO | 2019005774 A1 | 1/2019 |

OTHER PUBLICATIONS

Enterprise Neurotechnology Solutions; EMOTIV MN8; website available at: https://www.emotiv.com/workplace-wellness-safety-and-productivity-mn8/; last accessed Sep. 23, 2019.

* cited by examiner

WEARABLE AUDIO DEVICE WITH VAGUS NERVE STIMULATION

BACKGROUND

This disclosure generally relates to methods and systems for vagus nerve stimulation (VNS) provided by a wearable audio device such as a headset.

SUMMARY

The present disclosure is directed to methods and systems for vagus nerve stimulation by a wearable audio device worn by a user during the occurrence of a physiological event.

Generally, in one aspect, a method of providing vagus nerve stimulation (VNS) to a user is provided. The method includes the steps of: (1) collecting, by one or more sensors monitoring a user, one or more sets of physiological data; (2) determining, by a controller, an occurrence of a physiological event based on the one or more sets of physiological data; (3) stimulating, by a first earpiece of a wearable audio device worn by a user, a vagus nerve of the user with a VNS signal generated based on the controller determining the occurrence of the physiological event. The VNS signal may have an amplitude. The physiological condition may be an anxiety attack. The physiological condition may be a migraine headache.

According to an example, the method may further include the step of collecting, by the one or more sensors monitoring the user, one or more sets of additional physiological data.

According to an example, the method may further include the step of determining, by the controller, the physiological event has ended based on the one or more sets of additional physiological data.

According to an example, the vagus nerve may be continuously stimulated with the VNS signal until the controller has determined the physiological event has ended.

According to an example, the controller may be further configured to determine an intensity level of the physiological event. The amplitude of the VNS signal may be adjusted to correspond to the intensity level of the physiological event.

According to an example, the method may further include the step of programming, by the user via a user interface, the amplitude of the VNS signal.

According to an example, the method may further include the step of emitting, by an audio transducer of the wearable audio device, an audio signal corresponding to the physiological event.

Generally, in another aspect, a system for providing VNS to a user is provided. The system may include a wearable audio device. The wearable audio device may include a first earpiece. The first earpiece may include a first electrode configured to form a first electrical contact with an ear canal, tragus, or concha of a first ear of the user. The wearable audio device may further include a second electrode configured to form a second electrical contact with the user.

The system may further include one or more sensors configured to collect one or more sets of physiological data from a user. One of the sensors may be an electromyography sensor. One of the sensors may be a heart rate monitor. One of the sensors may be a galvanic skin response sensor. The wearable audio device may include one or more of the sensors.

The system may further include a controller configured to determine an occurrence of a physiological event based on the one more sets of physiological data. The controller may be electrically coupled to the first earpiece. The controller may be electrically coupler to the one or more sensors.

The first earpiece may be configured to deliver a VNS signal via the first electrode based on the controller determining the occurrence of the physiological event. The VNS signal may have an amplitude.

According to an example, the controller may be further configured to determine when the physiological event has ended based upon the one or more sets of physiological data. The first earpiece may be further configured to continuously deliver the VNS signal until the controller has determined the physiological event has ended.

According to an example, wherein the controller may be further configured to determine an intensity level of the physiological event. The amplitude of the VNS signal may be adjusted to correspond to the intensity level of the physiological event.

According to an example, the system may further include a user interface electrically coupled to the controller. The user interface may be configured for the user to program the amplitude of the VNS signal.

According to an example, the wearable audio device may further include an acoustic transducer. The acoustic transducer may be configured to emit an audio signal corresponding to the physiological event.

According to an example, the first earpiece further may include the second electrode.

According to an example, the second electrode may be configured to form the second electrical contract with the ear canal, tragus, or concha of the first ear of the user. Alternatively, the second electrode may form the second electrical contact with an ear canal, tragus, or concha of a second ear of the user. In a further alternative, the second electrode may form the second electrical contact on a back portion of an earlobe of the first ear.

Generally, in another aspect an earpiece for providing VNS to a user is provided. The earpiece may include a first electrode. The first electrode may be configured to form a first electrical contact with an ear canal, tragus, or concha of a first ear of the user. The first earpiece may be configured to deliver a VNS signal via the first electrode upon a controller determining an occurrence of a physiological event.

According to an example, the earpiece may further include a second electrode configured to form a second electrical contact with the user.

According to an example, the earpiece may further include one or more sensors configured to collect one or more sets of physiological data from the user.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various examples.

DETAILED DESCRIPTION

This disclosure is directed to methods and systems for vagus nerve stimulation (VNS) providing by a wearable audio device. VNS is an intervention that involves delivering electrical impulses to the vagus nerve of a user to induce a physiological response. The electrical impulses may be delivered via an ear canal, tragus, and concha of the user. VNS has been used to treat physiological disorders such as depression, insomnia, and tinnitus, among others.

This disclosure relates generally to incorporating VNS into wearable audio devices such as headphones, headsets, and earbuds which can be worn all day by a user. VNS may be applied via electrodes on earpieces (or other suitable configurations) to alleviate anxiety and/or depression. Headsets may be outfitted with sensors for monitoring user biometrics allowing VNS to be applied dynamically, e.g., when the onset of depression or anxiety is detected. Treatment can occur during normal use of the headset, such as while the user is listening to music.

The term "wearable audio device", as used in this application, is intended to mean a device that fits around, on, or in an ear and that radiates acoustic energy into or towards the ear. Wearable audio devices are sometimes referred to as headphones, earphones, earpieces, headsets, earbuds or sport headphones, and can be wired or wireless. Wearable audio devices can also include open ear wearable audio devices that deliver audio via bone conduction or pressure waves through the air. Examples of open ear audio devices are the Bose Frames audio sunglasses. A wearable audio device includes an acoustic driver to transduce audio signals to acoustic energy. The acoustic driver may be housed in an earcup, earbud, or other structure. While some of the figures and descriptions following may show a single wearable audio device having a single stand-alone unit having only one earpiece (including an acoustic driver), it should be appreciated that a wearable audio device may be a pair of earpieces. Each earpiece of the wearable audio device may be connected mechanically to another earpiece or headphone, for example by a headband and/or by leads that conduct audio signals to an acoustic driver in the ear cup or headphone. A wearable audio device may include components for wirelessly receiving audio signals. A wearable audio device may include components of an active noise reduction (ANR) system. Wearable audio devices may also include other functionality such as a microphone so that they can function as a headset.

The examples and implementations disclosed or otherwise envisioned herein can be utilized with any suitable earpiece. Examples of suitable earpieces include Bose® Sleepbuds™ (manufactured by Bose Corporation of Framingham, Mass.), ear tips, earbuds, in-ear headphones, over-the-ear headphones, noise-blocking earplugs, and hearing aids. However, the disclosure is not limited to these devices, and thus the disclosure and embodiments disclosed herein can encompass any earpiece configured to be placed at least partially within human ears.

Figure 1:
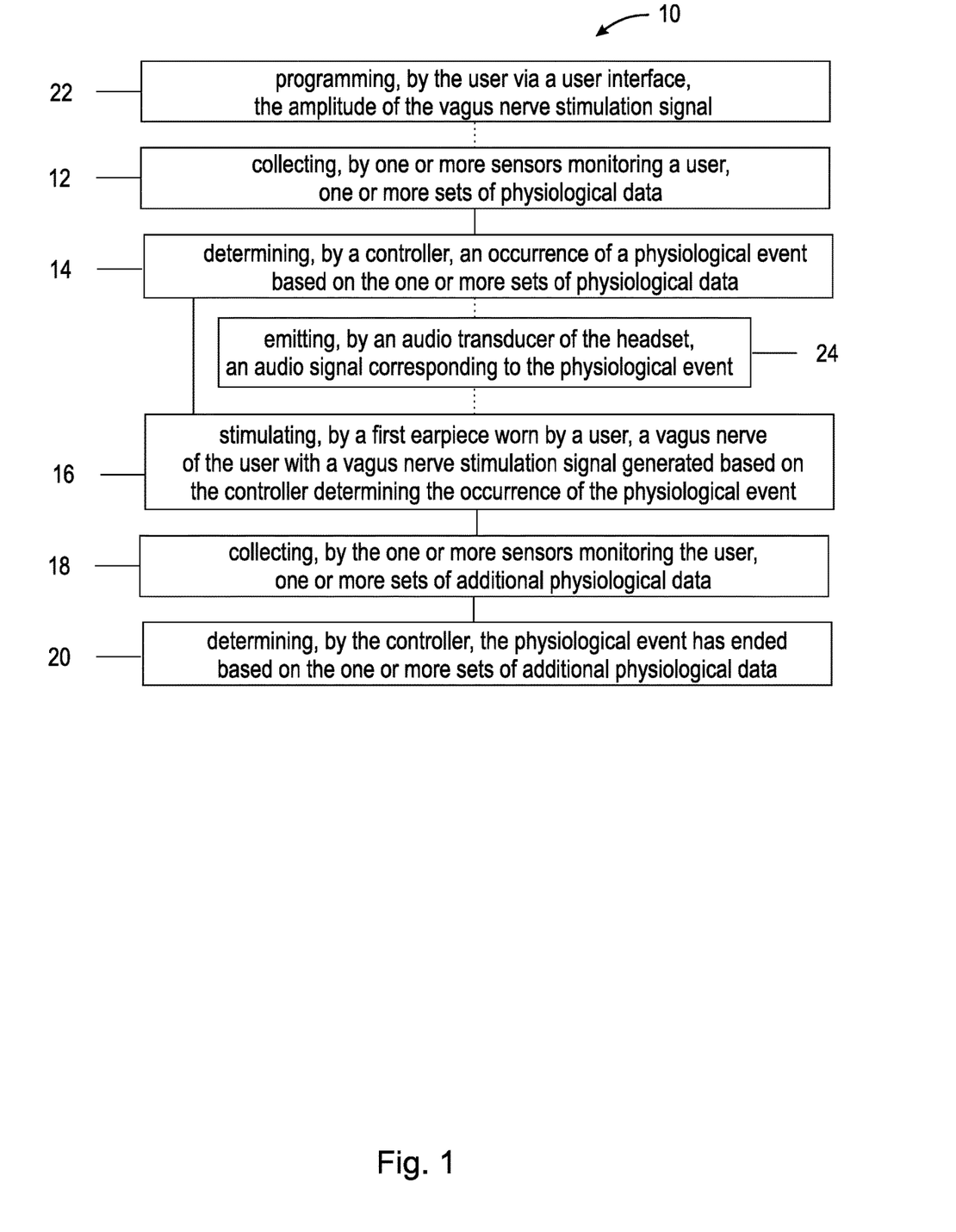
FIG. 1 is a flowchart of an example of a method of providing VNS to a user.

In one aspect, and with reference to FIG. 1, a method 10 of providing vagus nerve stimulation to a user is disclosed. The method 10 may include the step of collecting 12, by one or more sensors monitoring a user, one or more sets of physiological data. One of the sensors may be any type of sensor capable of capturing physiological data indicative of the occurrence of a physiological event, such as an anxiety attack or migraine headache. One of the sensors may be an electromyography sensor. One of the sensors may also be a heart rate monitor. One of the sensors may further be embedded into a head set worn by a user, such as on an earpiece or ear cup. One of the sensors may also be an external device apart from the headset.

The method 10 may further include the step of determining 14, by a controller, an occurrence of a physiological event based on the one or more sets of physiological data. The controller may also analyze additional data, such as information provided by the user via a user interface, in determining the occurrence of the physiological event. This step may also include determining the type (migraine, anxiety attack, etc.), severity, of expected duration of the event. Increased levels of anxiety may be indicated by a variety of biometrics, including, but not limited to, a reduction in heart rate variability, a reduction in skin conductance, an increase in breath rate combined with a decrease breath depth, or an increase in cortisol level.

The method 10 may further include the step of stimulating 16, by a first earpiece, a vagus nerve of the user with a VNS signal generated based on the controller determining the occurrence of the physiological event. The VNS signal may have an amplitude. The VNS signal may have other characteristics of an electronic signal, such as period, frequency, pulse width, duty cycle, etc.

The method 10 may further include the step of collecting 18, by the one or more sensors monitoring the user, one or more sets of additional physiological data. The additional physiological data may be of a similar or different type of physiological data as previously collected.

The method 10 may further include the step of determining 20, by the controller, the physiological event has ended based on the one or more sets of additional physiological data. The vagus nerve may be continuously stimulated with the VNS signal until the controller has determined the physiological event has ended. Upon this determination, the controller may alter or cease VNS treatment.

The controller may be further configured to determine an intensity level of the physiological event. The amplitude of the VNS signal may be adjusted to correspond to the intensity level of the physiological event. Additionally, other characteristics of the VNS signal may be adjusted in relation to the intensity of the physiological event. For example, if the intensity level is low, the amplitude of the VNS signal may also be low. Similarly, if the intensity level is high, the amplitude of the VNS signal may also be high.

The method 10 may further include the step of programming 22, by the user via a user interface, the amplitude of the VNS signal. The user interface may be any device capable of receiving input from a user, such as a smartphone. Additionally, other characteristics of the VNS signal may be adjusted via the user interface, such as period, frequency, pulse width, duty cycle, etc.

The method 10 may further include emitting 24, by an audio transducer of the wearable audio device, an audio signal corresponding to the physiological event. The audio signal may be an audio tone, an audio recording, or any other sound indicative of the occurrence of the physiological event.

Figure 2:
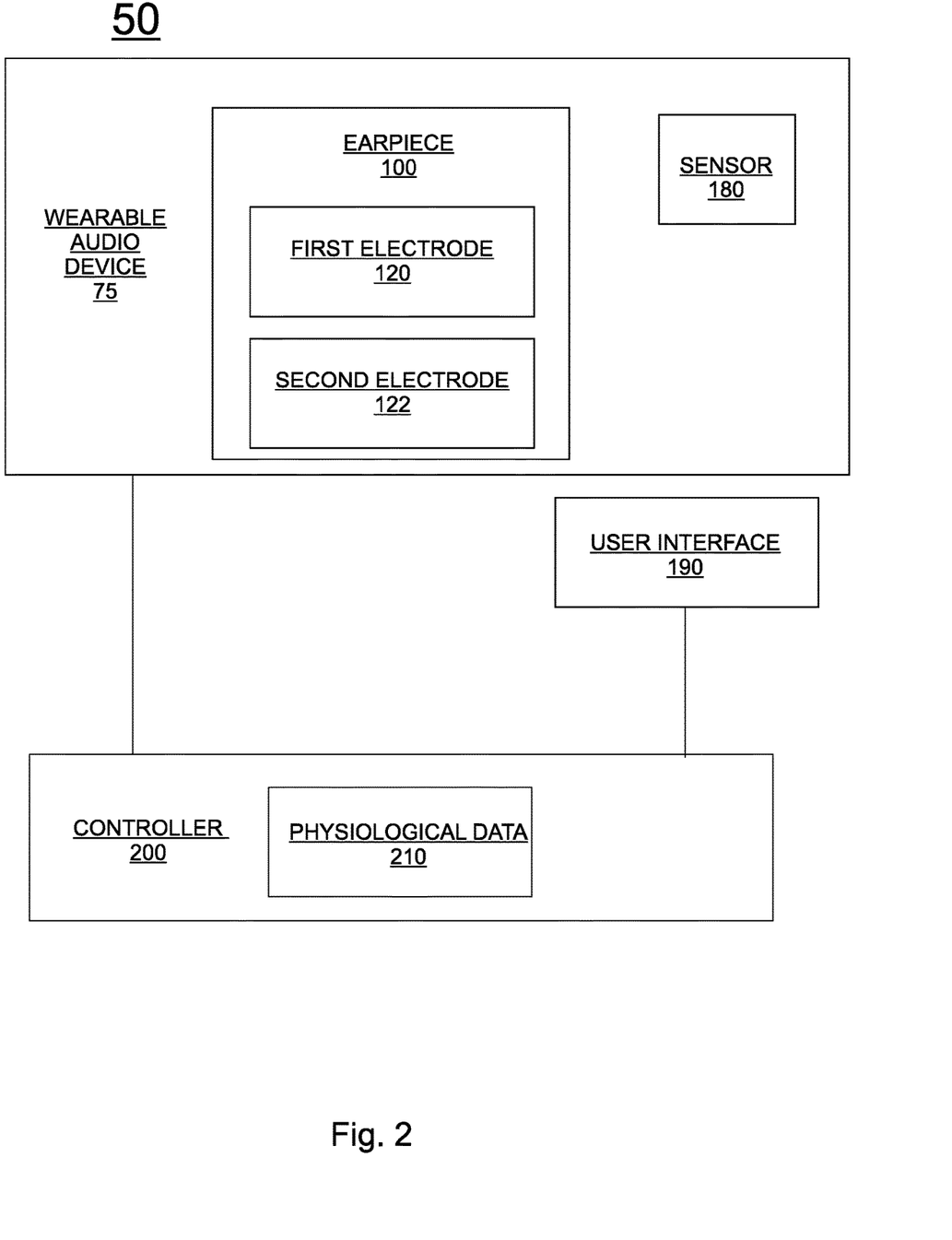
FIG. 2 is a schematic of a system for providing VNS to a user.

In another aspect, and with reference to FIG. 2, a system 50 for providing VNS to a user is provided. The system 50 may include a wearable audio device 75. The wearable audio device 75 may be on any type of device configured to be regularly worn by the user, such as ear tips, earbuds, in-ear headphones, over-the-ear headphones, noise-blocking earplugs, or hearing aids.

The wearable audio device 75 may include a first earpiece 100. The first earpiece 100 include a first electrode 120 configured to form a first electrical contact with an ear canal, tragus, and/or concha of a first ear of the user.

The wearable audio device 75 may further include a second electrode 122 configured to form a second electrical contact with the user. The second electrode 122 may be configured to form the second electrical contract with the ear canal, tragus, and/or concha of the first ear of the user. The second electrode 122 may be also configured to form the second electrical contact with an ear canal, tragus, and/or concha of a second ear of the user. In this configuration, the second electrode 122 may be incorporated into a second earpiece, such that current flows between the first electrode 120 in the first earpiece 100 and the second electrode 122 in the second earpiece. The second electrode 122 may be further configured to form the second electrical contact on a back portion of an earlobe of the first ear. The second electrode 122 may be incorporated into the first earpiece 100.

The system 50 may further include one or more sensors 180 configured to collect one or more sets of physiological data 210 from a user. One of the sensors 180 may be any type sensor capable of capturing physiological data 210 indicative of the occurrence of a physiological event, such as an anxiety attack or migraine headache. One of the sensors 180 may be an electromyography sensor. One of the sensors 180 may be a heart monitor. The heart monitor may be configured to measure heart rate and/or heart rate variability. One of the sensors 180 may be embedded into the wearable audio device, such as on an earpiece 100 or ear cup.

The system 50 may further include a controller 200 configured to determine an occurrence of a physiological event based on the one more sets of physiological data 210. The controller may be electrically coupled to the first earpiece 100 and the one or more sensors 180 via wired or wireless connection.

The first earpiece 100 may be configured to deliver a VNS signal via the first electrode 120 based on the controller 200 determining the occurrence of the physiological event. The VNS signal may have an amplitude. The VNS signal may have other characteristics of an electronic signal, such as period, frequency, pulse width, duty cycle, etc.

The controller 200 may be further configured to determine when the physiological event has ended based upon the one or more sets of physiological data 210. The first earpiece 100 may be further configured to continuously deliver the VNS signal until the controller 200 has determined the physiological event has ended. Alternatively, the controller 200 may simply alter, rather than cease, delivery of the VNS signal upon the determination the event has ended.

The controller 200 may be further configured to determine an intensity level of the physiological event. The amplitude of the VNS signal may be adjusted to correspond to the intensity level of the physiological event. Additionally, other characteristics of the VNS signal may be adjusted in relation to the intensity of the physiological event. For example, if the intensity level is low, the amplitude and frequency of the VNS signal may also be low. Similarly, if the intensity level is high, the amplitude and frequency of the VNS signal may also be high.

The system 50 may further include a user interface 190 electrically coupled to the controller 200. The user interface 190 may be any device capable of receiving input from a user, such as a smartphone. The user interface 190 may be configured for the user to program the amplitude of the VNS signal. Additionally, other characteristics of the VNS signal may be adjusted via the user interface, such as period, frequency, pulse width, duty cycle, etc. The user interface may be coupled to the controller 200 by wired or wireless connection.

The system 50 may be embodied using a variety of different system architectures. In a first example, the system 50 may be a standalone device. In this example, all aspects of the system 50, including earpieces 100 and/or other acoustic devices, sensors 180, controllers 200, storage devices, etc., are all incorporated into a single wearable audio device 75. The wearable audio device 75 may be configured to connect to a cloud computing system. The cloud connection may be direct. The cloud connection may be indirect via smartphone or other device. Connection to the cloud may enable the wearable audio device 75 to upload sensor data and/or usage data. Connection to the cloud may also enable the wearable audio device 75 to download updates or new features for the controller 200.

In a second example architecture for system 50, earpieces 100 and/or other acoustic devices, sensors 180, and a Bluetooth or other radio connection may be incorporated into the wearable audio device 75. The controller 200 and its associated processors and sensors 180 may be incorporated into a smartphone or other ancillary device. The sensors 180 in the smartphone may be configured to provide information (contextual or otherwise) to an algorithm to determine the occurrence (or impending occurrence) of a physiological event. The algorithm may make its determination based on date, time of day, weather, location of the user, and/or media access control (MAC) addresses of other smartphones near the user. For example, if the smartphone detects the user is commuting to work and stuck in traffic, it may use this contextual information to predict a higher likelihood of a physiological event. The algorithm determining the occurrence of a physiological event could also predict the onset of such events by applying machine learning to data collected from the sensors 180 on the wearable audio device 75 and contextual information captured by the smartphone.

In a third example architecture for system 50, earpieces 100 and/or other acoustic devices, sensors 180 (biometric and/or physiological), and a Bluetooth or other radio interface may be incorporated into the wearable audio device 75. The controller 200 and its associated processors may be located in the cloud. A smartphone may connect the wearable audio device 75 to the controller 200 in the cloud. The smartphone may also provide additional contextual data to the controller 200 in the cloud. In this example, the controller 200 may apply machine learning across data collected from multiple users to better predict the onset of a physiological event and apply VNS.

Figure 3:
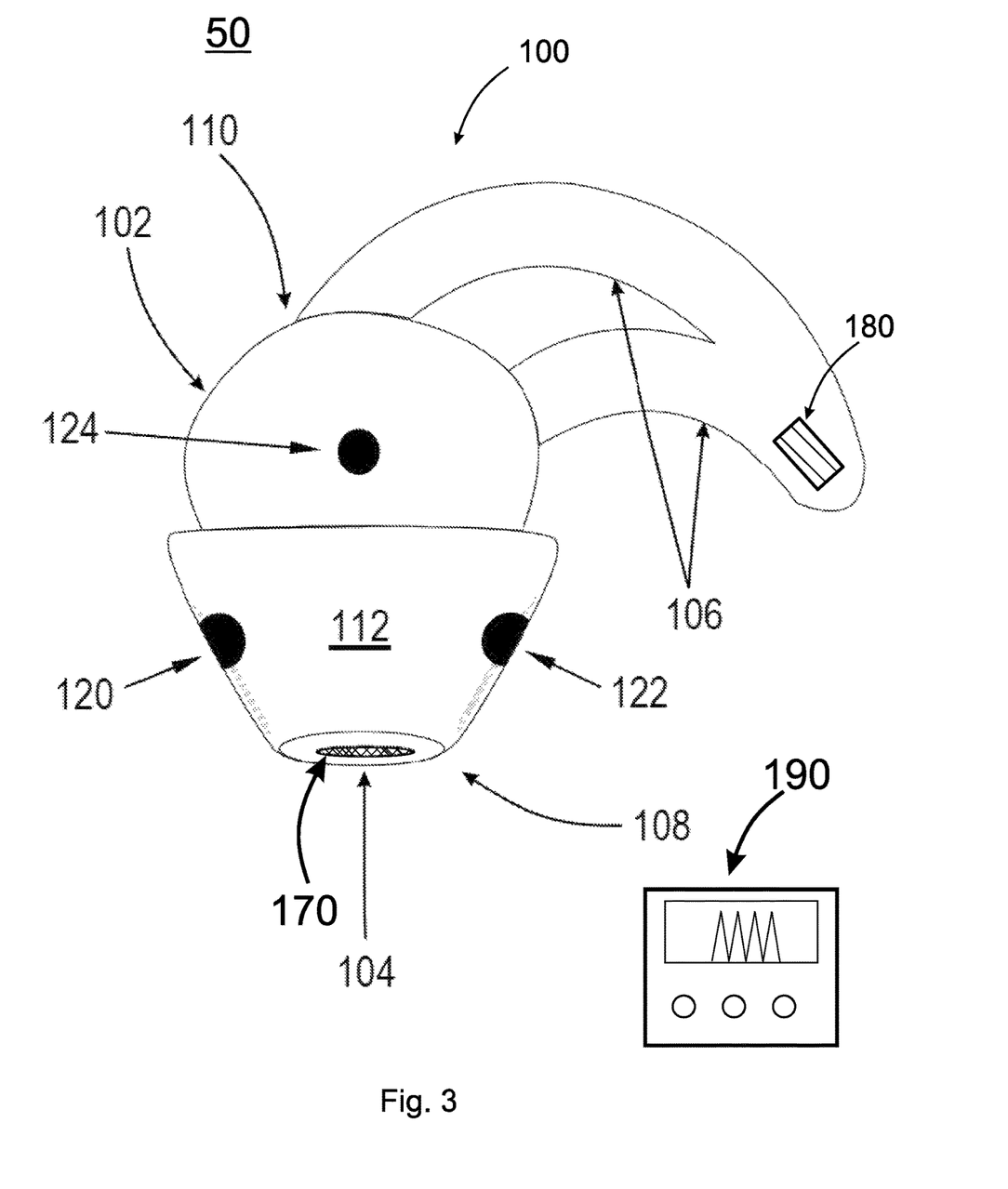
FIG. 3 is an example earpiece.

FIG. 3 illustrates an exemplary earpiece 100 for providing VNS to a user. The earpiece 100 includes an ear tip that is configured to fit at least partially into a person's ear canal and a retaining structure configured to hold the ear tip in place when worn. The earpiece 100 may include a first electrode 120 configured to form a first electrical contact with an ear canal, tragus, and/or concha of a first ear of the user. The first earpiece 100 may be configured to deliver a VNS signal via the first electrode 120 upon a controller 200 determining an occurrence of a physiological event. The earpiece 100 may further include a second electrode 122 configured to form a second electrical contact with the user. The earpiece 100 may further include one or more sensors 180 configured to collect one or more sets of physiological data 210 from the user. The earpiece 100 may further include an acoustic transducer 170. The acoustic transducer 170 may be disposed within earpiece 100. The acoustic transducer 170 may be configured to emit an audio signal corresponding to the physiological event.

Earpiece 100 can include body 102, and hollow passage 104, and retaining legs 106. Although FIG. 3 shows retaining legs 106 as one embodiment of a retaining structure, this disclosure is not limited to such a configuration. Any type of retaining structure is contemplated. Alternatively, the retaining structure can be omitted altogether. The retaining legs 106 are optional.

Body 102 includes first end 108 and second end 110 opposite the first end 108. Second end 110 is proximate to the retaining legs 106. Body 104 further includes inner wall 107 extending between the first end 108 and the second end 110. Inner wall 107 defines and surrounds hollow passage 104 which can be configured to conduct sound waves. Body 102 also includes outer wall 112 connected to the inner wall 107 at the first end 108. Outer wall 112 tapers away from the inner wall 107 toward the second end 110. In example aspects, outer wall 112 is frustoconical in shape. As shown in FIG. 3, outer wall 112 tapers toward the second end 110 but does not necessarily reach the second end 110. In alternate embodiments not shown, outer wall 112 could extend to the second end 110 or beyond second end 110. Body 102 can be made of any suitable soft, flexible materials, including, for example, silicone, polyurethane, polynorbornene (e.g., Norsorex® material available from D-NOV GmbH of Vienna, Austria), thermoplastic elastomer (TPE), and/or fluoroelastomer.

Earpiece 100 includes electrically conductive elements 120, 122, and 124, which function as electrodes when positioned to contact skin within the ear, which generally is a stable environment offering good electrical and/or mechanical contact between skin and electrodes. Although FIG. 3 shows one particular configuration of an ear tip with electrically conductive elements 120 and 122 arranged on opposite sides of an outer surface of outer wall 112 (configured to fit at least partially into a person's ear canal), and electrically conductive element 124 arranged on body 102, this disclosure is not limited to such a configuration, and any number of electrically conductive elements can be placed in any configuration on earpiece 100 as long as the electrically conductive elements are arranged to contact skin and provide VNS within the ear when the earpiece is worn by a user. It should be appreciated that only two electrodes may be active in one system. However, in certain embodiments, multiple electrically conductive elements may be used to function as a single electrode when electrically connected together.

Examples of electrically conductive elements include a metal pad, metal button, metal foils (e.g., gold, silver), metal-salt hybrids (e.g., silver/silver-chloride), polymeric composites (e.g., rubbers compounded with conductive fillers such as carbon black, carbon nanotubes, graphene, silver, glass-coated silver), intrinsically conductive polymers (e.g., poly(3,4-ethylenedioxythiophene) polystyrene sulfonate or PEDOT:PSS), and/or conductive fabric (e.g., fabrics with conductive yarns, fabrics coated with conductive materials).

Electrically conductive elements 120, 122, and/or 124 can be used to deliver an electrical signal to the ear, for example, for use in VNS. Electrically conductive elements 120, 122, and/or 124 can also function as physiological electrodes for detecting bioelectrical signals of an individual, including, for example, electroencephalogram (EEG), electrooculogram (EOG), electrocardiography (ECG), and electromyogram (EMG) signals, and may also be used to detect pulse rate, respiration rate, body temperature, sweat levels, and glucose, among other health parameters. Accordingly, electrically conductive elements 120, 122, and 124 may be used in place of or in conjunction with sensor 180.

Earpiece 100 may include an embedded integrated circuit, for example, inside the body 102. In examples, earpiece 100 is communicably coupled with an integrated circuit that is separate and remotely located, for example, in a computer or a mobile device. The integrated circuit can include a data processor, a memory, and a communication processor. Commands to be executed by the processor can be obtained via the communication processor. The communication processor facilitates wired or wireless communication for earpiece 100 and can be facilitated via one or more antennas, for example. The communication processor can facilitate communication with one or more networks or other devices, for example, by using wireless methods that are known, including but not limited to Wi-Fi, Bluetooth, 3G, 4G, LTE, and/or ZigBee, among others. Earpiece 100 can further include an embedded power source (e.g., a battery) required to carry out various functionalities involving the integrated circuit and the one or more electronic components described herein.

The above-described examples of the described subject matter can be implemented in any of numerous ways. For example, some aspects may be implemented using hardware, software or a combination thereof. When any aspect is implemented at least in part in software, the software code can be executed on any suitable processor or collection of processors, whether provided in a single device or computer or distributed among multiple devices/computers.

The present disclosure may be implemented as a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some examples, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to examples of the disclosure. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various examples of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While several inventive examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive examples described herein. It is, therefore, to be understood that the foregoing examples are presented by way of example only and that, within the scope of the appended claims and equivalents thereto, inventive examples may be practiced otherwise than as specifically described and claimed. Inventive examples of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Other implementations are within the scope of the following claims and other claims to which the applicant may be entitled.

What is claimed is:

1. A method of providing vagus nerve stimulation to a user, comprising the steps of:
    collecting, by one or more sensors monitoring a user, one or more sets of physiological data;

determining, by a controller, an occurrence of a physiological event based on the one or more sets of physiological data;

emitting, by an audio transducer, an audio signal indicative of the occurrence of the physiological event; and beginning stimulation, by a first earpiece worn by a user, of a vagus nerve of the user with a vagus nerve stimulation signal generated based on the controller determining the occurrence of the physiological event, wherein the vagus nerve stimulation signal has an amplitude.

2. The method of claim 1, further comprising the step of collecting, by the one or more sensors monitoring the user, one or more sets of additional physiological data.

3. The method of claim 2, further comprising the step of determining, by the controller, the physiological event has ended based on the one or more sets of additional physiological data.

4. The method of claim 3, wherein the vagus nerve is continuously stimulated with the vagus nerve stimulation signal until the controller has determined the physiological event has ended.

5. The method of claim 1, wherein the controller is further configured to determine an intensity level of the physiological event.

6. The method of claim 5, wherein the amplitude of the vagus nerve stimulation signal is adjusted to correspond to the intensity level of the physiological event.

7. The method of claim 1, further comprising the step of programming, by the user via a user interface, the amplitude of the vagus nerve stimulation signal.

8. The method of claim 1, wherein the physiological event is a migraine or anxiety attack.

9. A system for providing vagus nerve stimulation to a user, comprising:

a wearable audio device, comprising:
  a first earpiece, wherein the first earpiece comprises a first electrode configured to form a first electrical contact with an ear canal, tragus, or concha of a first ear of the user;
  a second electrode configured to form a second electrical contact with the user;
one or more sensors configured to collect one or more sets of physiological data from a user; and
a controller configured to determine an occurrence of a physiological event based on the one more sets of physiological data, wherein the controller is electrically coupled to the first earpiece and the one or more sensors; and
an acoustic transducer configured to emit an audio signal indicative of the occurrence of the physiological event;
wherein the first earpiece is configured to begin delivery of a vagus nerve stimulation signal via the first electrode based on the controller determining the occurrence of the physiological event, wherein the vagus nerve stimulation signal has an amplitude.

10. The system of claim 9, wherein the controller is further configured to determine when the physiological event has ended based upon the one or more sets of physiological data.

11. The system of claim 10, wherein the first earpiece is further configured to continuously deliver the vagus nerve stimulation signal until the controller has determined the physiological event has ended.

12. The system of claim 9, wherein the controller is further configured to determine an intensity level of the physiological event.

13. The system of claim 12, wherein the amplitude of the vagus nerve stimulation signal is adjusted to correspond to the intensity level of the physiological event.

14. The system of claim 9, further comprising a user interface electrically coupled to the controller.

15. The system of claim 14, wherein the user interface is configured for the user to program the amplitude of the vagus nerve stimulation signal.

16. The system of claim 9, wherein the physiological event is a migraine or anxiety attack.

17. The system of claim 9, wherein the first earpiece further comprises the second electrode.

18. The system of claim 17, wherein the second electrode is configured to form the second electrical contact with the ear canal, tragus, or concha of the first ear of the user.

19. An earpiece for providing vagus nerve stimulation to a user, wherein the earpiece is in electronic communication with a controller configured to determine an occurrence of a physiological event, the earpiece comprising a first electrode configured to form a first electrical contact with an ear canal, tragus, or concha of a first ear of the user, wherein the first earpiece is configured to begin delivery of a vagus nerve stimulation signal via the first electrode upon the controller determining the occurrence of the physiological event, and wherein the earpiece is further configured to emit, by an audio transducer, an audio signal indicative of the occurrence of the physiological event.

20. The earpiece of claim 19, wherein the physiological event is a migraine or anxiety attack.

* * * * *